(12) United States Patent
Zhou et al.

(10) Patent No.: US 9,505,910 B2
(45) Date of Patent: Nov. 29, 2016

(54) MODIFIED DIPHENYLMETHANE DIISOCYANATE (MDI) BIURET CURING AGENT AND PREPARATION METHOD THEREOF

(75) Inventors: Jianming Zhou, Wuhan (CN); Shaoqun He, Wuhan (CN)

(73) Assignee: J&H Xiangyang Chemical Co., Ltd., Wuhan, Hubei (CN)

( * ) Notice: Subject to any disclaimer, the term of this patent is extended or adjusted under 35 U.S.C. 154(b) by 247 days.

(21) Appl. No.: 14/352,232

(22) PCT Filed: Jun. 12, 2012

(86) PCT No.: PCT/CN2012/076778
§ 371 (c)(1),
(2), (4) Date: Apr. 16, 2014

(87) PCT Pub. No.: WO2013/056559
PCT Pub. Date: Apr. 25, 2013

(65) Prior Publication Data
US 2014/0252269 A1    Sep. 11, 2014

(30) Foreign Application Priority Data

Oct. 20, 2011  (CN) .......................... 2011 1 0320518
Nov. 25, 2011  (CN) .......................... 2011 1 0380099

(51) Int. Cl.
*C08K 5/29*     (2006.01)
*C08K 5/01*     (2006.01)
(Continued)

(52) U.S. Cl.
CPC .............. *C08K 5/29* (2013.01); *C07C 275/62* (2013.01); *C08G 18/302* (2013.01);
(Continued)

(58) Field of Classification Search
CPC .......... C08K 5/29; C08K 5/01; C08K 5/103; C08K 5/07; C08G 18/321; C08G 18/7831; C08G 18/7671; C08G 18/302; C08G 18/3206; C08G 18/42; C08G 18/48; C09D 175/04; C07C 275/62
See application file for complete search history.

(56) References Cited

U.S. PATENT DOCUMENTS 2,145,392 A * 1/1939 Harmon ............ C07C 273/1881
                                                    564/38
4,367,294 A * 1/1983 Hahn .................... C08G 18/544
                                                    521/136

(Continued)

FOREIGN PATENT DOCUMENTS

CN       1175965 A      3/1998
CN    101775120 A      7/2010
EP       2272883 A1     1/2011

*Primary Examiner* — Peter F Godenschwager
*Assistant Examiner* — Andrew J Oyer
(74) *Attorney, Agent, or Firm* — Hayes Soloway, P.C.

(57) ABSTRACT

Provided are a modified diphenylmethane diisocyanate (MDI) biuret curing agent and preparation method thereof, the curing agent being prepared by reacting dibasic alcohol, water and MDI in an organic solvent. The preparation method includes the steps of: firstly, using the dibasic alcohol to modify a part of MDI, dividing the metered water into multiple parts, and adding the water by multiple times; after adding the first part of water, reacting firstly under 70-100° C., then heating up to 120-140° C. for reaction; secondly, lowering the temperature to 70-100° C., adding the second part of water; and repeating the above processes until all the metered water is added, to produce the MDI curing agent with partial biuret structure. The curing agent is mainly used as the curing agent of polyurethane coating Infrared spectrogram of a laboratory sample of the invention and adhesive agent, and has a higher NCO percentage and a slower curing speed than that of common MDI prepolymer curing agents.

6 Claims, 1 Drawing Sheet

(51) Int. Cl.
*C08K 5/103* (2006.01)
*C08K 5/07* (2006.01)
*C08G 18/32* (2006.01)
*C09D 175/04* (2006.01)
*C08G 18/30* (2006.01)
*C08G 18/76* (2006.01)
*C08G 18/48* (2006.01)
*C08G 18/42* (2006.01)
*C07C 275/62* (2006.01)
*C08G 18/78* (2006.01)

(52) U.S. Cl.
CPC ..... *C08G 18/3206* (2013.01); *C08G 18/3212* (2013.01); *C08G 18/42* (2013.01); *C08G 18/48* (2013.01); *C08G 18/7671* (2013.01); *C08G 18/7831* (2013.01); *C08K 5/01* (2013.01); *C08K 5/07* (2013.01); *C08K 5/103* (2013.01); *C09D 175/04* (2013.01)

(56) References Cited

U.S. PATENT DOCUMENTS 6,838,542 B1 * 1/2005 Slack ................. C08G 18/4825
252/182.21
7,022,874 B2 * 4/2006 Bruchmann .......... C07C 265/14
560/335

* cited by examiner

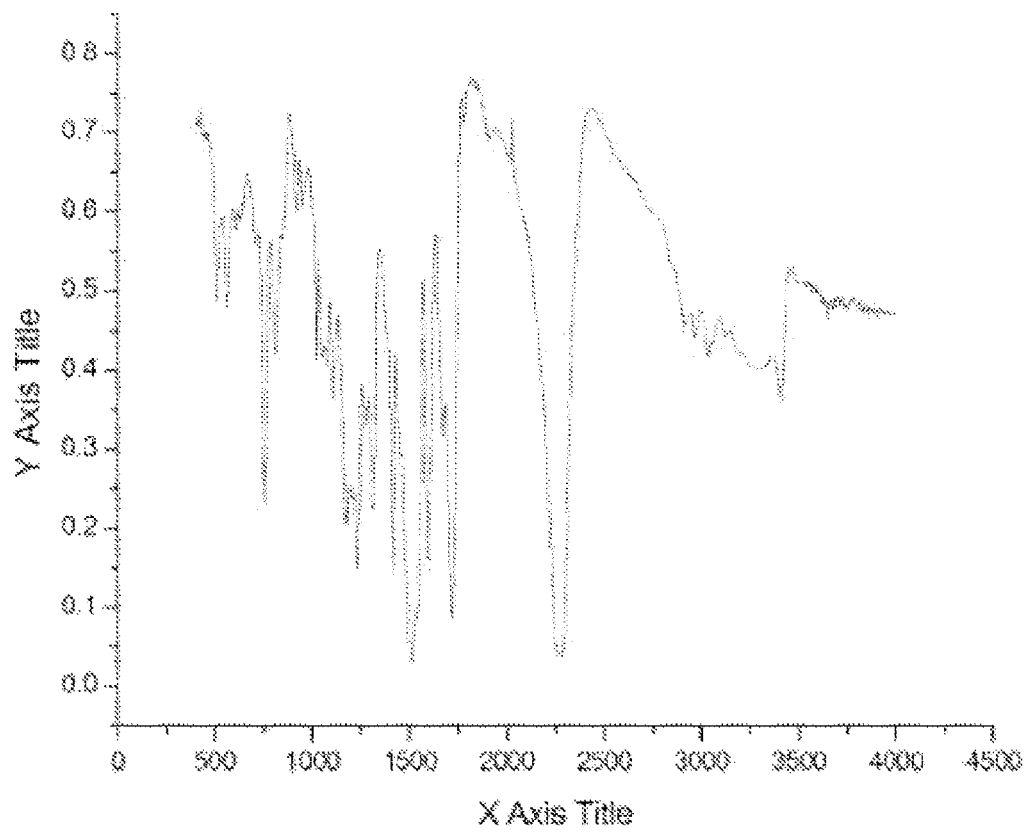
Infrared spectrogram of a laboratory sample of the invention

MODIFIED DIPHENYLMETHANE DIISOCYANATE (MDI) BIURET CURING AGENT AND PREPARATION METHOD THEREOF

FIELD OF THE INVENTION

The present invention relates to preparation of an aromatic polyisocyanate through a water method, and in particular, to the preparation of a modified biuret curing agent by water, dibasic alcohol and diphenylmethane diisocyanate (MDI) and a preparation method thereof.

BACKGROUND OF THE INVENTION

At present, a prepolymer (hereinafter referred to as a TDI curing agent) of virulent toluene diisocynate (TDI) and trimethylolpropane (TMP) is mainly used as a curing agent for double component polyurethane coatings, adhesive agents and printing ink. People have paid more and more attention on the environmental pollution problem caused by residual monomers of the TDI curing agent. Overseas manufacturers mostly adopt a rotary thin film evaporation technology to reduce the content of free TDI monomers; however, domestic enterprises do not handle the free TDI monomers due to the complex process engineering and expensive devices; therefore, the content of the free TDI monomers is generally larger than 2% in average, and even as high as 10% sometimes. In recent years, a number of works have been done on developing an environment friendly MDI curing agent to substitute the TDI curing agent in China. Some invention patents have been disclosed and some MDI curing agent products have been launched in the market. However, some problems to be resolved still exist in the process of replacing the TDI curing agent for use, wherein the prominent problems are that the NCO percentage of the MDI curing agent is lower than that of the TDI curing agent and the curing speed is faster, which are not suitable for application in some specific conditions, and obstruct the spreading and popularization of the MDI curing agent.

China patents CN101230124B and CN101440149B disclose a method to prepare an MDI prepolymer curing agent having high solid content and low viscosity by using dibasic alcohol to modify 4,4'-MDI firstly, and then solely or be mixed with an isomer 4,2'-MDI in any weight ratio, and react with trimethylolpropane. Although the NCO percentage of the curing agent can be improved and the curing speed can be reduced through selecting dibasic alcohol having different molecular weights and structures, the regulating degree is limited and the problems of low NCO percentage (9~15%), and faster solidification rate still exist, which affect some application ranges and construction pot life.

The MDI prepolymer curing agent prepared by China patent CN1357558A by adopting trimethylolpropane, castor oil and 4,4'-MDI and the MDI prepolymer curing agent prepared by China patent CN1357559A by adopting trimethylolpropane, 4,2'-and 4,4'-MDI both have the technical defects of low solid content of a curing agent system, lower NCO percentage (10~15%) and higher content of free isocyanate monomers in the system, which are easy to cause fast solidification in the prophase of construction and slow solidification in the anaphasis of construction.

Generally, the NCO percentages of the TDI prepolymer curing agents sold in the market are 16~48% (as high as 19% theoretically, because a polymer consumes partial NCO), the NCO percentages of the MDI prepolymer curing agents of the foregoing several patents are all lower than the number. Low NCO percentages of the curing agent will increase the comprehensive cost of the user, bringing difficulty spreading and applying the MDI curing agent. Analytically, the reason why the NCO percentage of the MDI prepolymer curing agent is lower than that of the TDI prepolymer curing agent is that the molecular weight of the MDI is larger than that of the molecular weight, resulting in that the NCO content of unit quantity is reduced after the MDI is prepolymerized with same trimethylolpropane. Therefore, the polybasic alcohol molecular weight of the prepolymer shall be reduced as much as possible so as to improve the percentage of the MDI curing agent; thus, the inventor gets an idea of replacing the polybasic alcohol by water to react with the MDI for trying to prepare MDI biuret triisocyanate.

Since 1958, people have just known two preparation methods of aliphatic isocyanate having a biuret structure. The first one is the so-called water method, wherein aliphatic diisocyanate is reacted with water to form urea and subsequently form biuret, and HDI biuret has been produced industrially. The second method is the so-called aliphatic diisocyanate/aliphatic diamine method, wherein urea is directly prepared through isocyanate and amine, and then a biuret reaction is performed. A "Method for Preparing Polyisocyanates Having Biuret Structure" disclosed by China patent CN1188445C applied by Germany Bayer is just a method of continuously preparing the polyisocyanates having a biuret structure by using aliphatic and/or cycloaliphatic diisocyanate and aliphatic and/or diisocyanate diamine. So far, the polyisocyanates having a biuret structure are all prepared by using aliphatic diisocyanate, and there is no report about using aromatic diisocyanate to prepare the biuret polyisocyanates.

Since an induction effect exists between two —NCO groups on a benzene ring, the activity of the aromatic diisocyanate are higher than that of the aliphatic diisocyanate, and the manufacturing difficulty is enlarged, which is a technical problem to be solved by the international persons in polyurethane industry.

The present invention, directing at preparing an MDI biuret structure triisocyanate with water, proposes a preparation method of a modified aromatic biuret, which preferably solves the problems of the existing MDI prepolymer curing agents.

SUMMARY OF THE INVENTION

The design idea of the present invention is to firstly use dibasic alcohol to modify part of 4,4'-MDI molecular structures, change symmetrical molecular structures thereof, reduce the activity of an NCO functional group thereof, produce activity differences among the molecule in a system, so as to produce different speeds while being reacted with water subsequently, thus avoiding the generation of "polyurea" slag.

BRIEF DESCRIPTION OF THE DRAWINGS

FIG. 1 is an infrared spectrogram of a laboratory sample of the invention.

DETAILED DESCRIPTION OF THE EMBODIMENTS

The present invention may be realized through following measures: firstly using dibasic alcohol to modify part of the MDI, and then adopting a circular reaction process of adding water by multiple times and reacting step-by-step to prepare the modified MDI biuret curing agent.

The present invention is a mixed prepolymer produced by using an organic solvent as a solvent and performing a reaction among dibasic alcohol, water and diphenylmethane diisocyanate, comprising a dibasic alcohol modified MDI structure and a biuret structure, which has a schematic unit cell structure formula as follows:

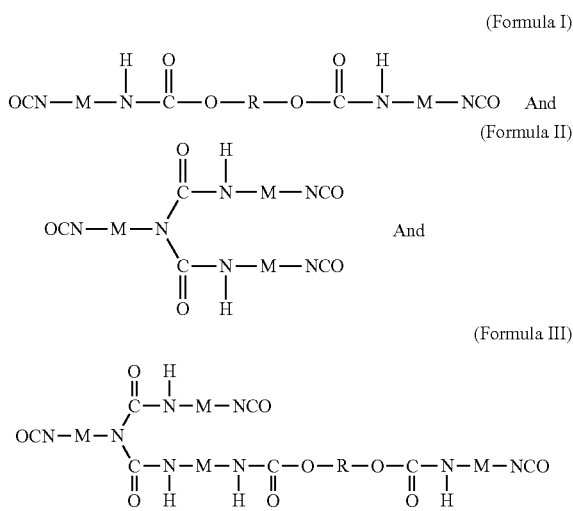

Where, M is

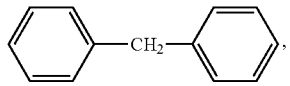

and R is a structure of the part of the dibasic alcohol excluding the hydroxyl radical.

The feeding ratios of each reactant in the curing agent are as follows: in the first step of the reaction, the molar ratio between the dibasic alcohol and the MDI is 0.05~0.2:1; in the second step of the reaction, the molar ratio between the water and the remaining MDI after the first step of the reaction is 1:3~3.2.

Since the mole number of the feeding ratio in the first step of the reaction is greatly larger than the mole number of the dibasic alcohol, the hydroxyl radicals at the two ends of the dibasic alcohol molecule are all respectively reacted with the MIR That is to say, one mole of dibasic alcohol is reacted with two moles of MDI; therefore, the remaining mole number after the first step of the reaction as described in the second step of the reaction (namely the MDI mole number not participating in the first step of the reaction) is the difference result of subtracting two times of the mole number of the dibasic alcohol from the MDI mole number fed in the first step of the reaction.

The product indexes of the curing agent are as follows, where the following contents are weight percentages:
(1) appearance: buff transparent liquid;
(2) solid content:50~75%;
(3) NCO content:12~18%;
(4) store period: half year.

The preparation method of the present invention and the steps thereof include:

a, adding MDI and an organic solvent into a reaction kettle, stirring uniformly, adding dehydrated dibasic alcohol for reaction at a room temperature for 0.5~2 hours, then heating up to 60° C., reacting under 60 to 90° C. for 1~4 hours, to obtain an MDI-modified product;

b, dividing the metered water into multiple parts, and adding the water by multiple times; controlling the temperature in the reaction kettle within 70~100° C. temperature, dropwise adding the first part of water, and reacting for 0.5~2 hours, then heating up to 120~140° C., and reacting for 0.5~2 hours; lowering the temperature to 70~100° C., dropwise adding the second part of water, repeating the above process until all the metered water is added, reacting for 0.5~2 hours, then heating up to 120~140° C. and reacting for 1~5 hours, where during this period, the reaction degree is monitored by sampling the reactants to detect the NCO percentage, and the reaction ends when the NCO content tends to be stable and approaches to a theoretical value; and c, lowering the temperature to 60° C., adding an organic solvent according to the product solid content requirements, stirring uniformly, and discharging to obtain the modified MDI biuret curing agent.

In the step a (namely the first step of the reaction) of the present invention, as the activity of the 4,4'-MDI in an MDI isomer is highest, when excessive MDI is reacted with dibasic alcohol, the 4,4'-MDI is mainly reacted with the dibasic alcohol to generate an MDI-modified product, which has a chemical reaction formula as follows:

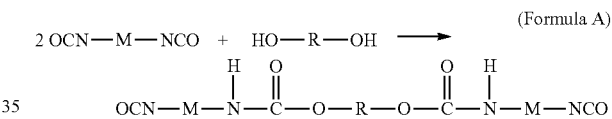

(Formula A)

Where, M is

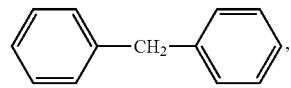

and R is a structure of the part of the dibasic alcohol excluding the hydroxyl radical.

The generation of the MDI-modified product changes the symmetrical molecular structure of the 4,4'-MDI, and reduces the activity of few functional groups, which causes differences between the molecules and the NCO groups in a system, and provides speed selectivity for subsequent reaction with the water.

In step b (namely the second step of the reaction), the metered water is divided into multiple parts, and then a circular reaction process of adding water by multiple times and reacting step-by-step to prepare the modified MDI biuret curing agent is also for the purpose of avoid "polyurea" slag from generating; meanwhile, a relative local environment with excessive MDI in the system is formed, which is beneficial for performing the reaction towards the direction of generating biuret.

The temperature in the reaction kettle is controlled within 70~100° C., and the first part of water is added to react for 0.5~2 hours; during this period, the water is firstly reacted with the —NCO group having high activity to generate primary amine which has very high activity and can be quickly reacted with the MDI to generate ureido diisocyanate. The reaction speed between the —NCO group having low activity and the water is slightly slow, thus forming a successively reaction sequence between the water and different —NCO groups, so that the reaction speed of different active molecules in the system are ordered, thus being capable of effectively avoiding "polyurea" slag from generating. Heating up to 120~140° C. and reacting for 0.5~2 hours refer to that the ureido diisocyanate is reacted with the MDI or the MDI-modified product to generate triisocyanate having a biuret structure (referred to as biuret), which is beneficial for the uniform performing of the biuret reaction in the second stage due to the homogeneity of the reaction speed in the system during the first stage, and is uneasy to generate a polymer A chemical reaction formula thereof is as follows:

Step 1, the MDI or the MDI-modified product is reacted with the water to generate primary amine.

OCN-M-NCO—H₂O—H₂N-M-NCO—O₂, (Formula B 1)

The primary amine is extremely easy to react with the MDI or the MDI-modified product to generate the ureido diisocyanate.

(Formula B2)

Step 2, the ureido diisocyanate is then reacted with the MDI and the MDI-modified product to generate biuret.

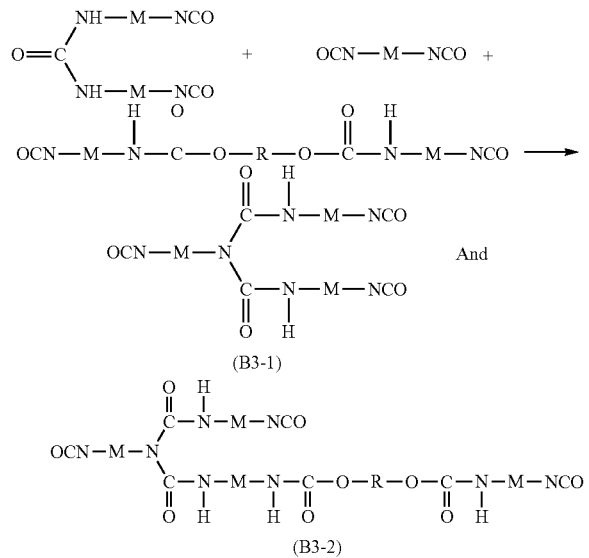

(B3-1)

(B3-2)

Where, M is

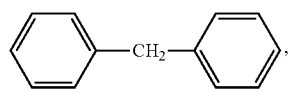

M is

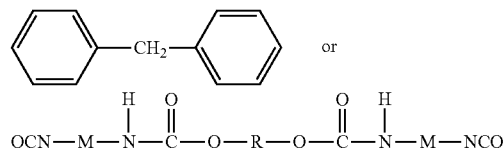

R is a structure of the part of the dibasic alcohol excluding the hydroxyl radical.

(Formula B3)

It can be seen from the reaction formula (formula B3) that the major products are biuret (B3-1) and (B3-2) as well as the MDI-modified product (the part in the products of reaction formula A that does not participate in the biuret reaction), few polymers, and the like.

The first part of water is added according to the present invention; after reacting at low temperature (70~100° C.) and high temperature (120~140° C.), the temperature is lowered to 70~100° C. then, and the second part of water is added; the process after adding the first part of water is circulated until all the metered water is added and the above process is completely carried out. The process of adding the water by multiple times and reacting at low temperature and high temperature step-by-step is to form a local environment having relatively excessive MDI in the system during different stages, which is beneficial for the generation of mono molecule biuret, as well as avoiding and reducing the generation of polymers.

The reaction of the present invention ends when the final part of water is added and the last process is circulated, and the reaction is continued at 120~140° C.; where during this period, whether the reaction shall be ended is determined by sampling the reactants to detect the NCO percentage, and the reaction ends when the NCO content does not reduce, tends to be stable and approaches to a theoretical value.

The product of the present invention is relatively clear and transparent, has no white slag, has low viscosity and a general solid content of 75%, where the viscosity is only 1500~5000 mpa·s (25° C.), thus greatly reducing the dosage of the organic solvent.

The present invention may regulate the NCO percentage of the product by selecting different dibasic alcohols and dosages thereof as well as water amount added, where the NCO percentage may be as high as 18%, which is equivalent to the NCO percentage of the TDI curing agent.

The product of the present invention has favorable storage stability and solvent dilution as well as slower room temperature curing speed.

In step a of the present invention, the MDI is one or a mixture of at least two of 4,4'-MDI, 4,2'-MDI and 2,2'-MDI in any weight ratio.

In step a of the present invention, the ratio among the 4,4'-MDI, the 4,2'-MDI and the 2,2'-MDI may be that the 4,4'-MDI: 4,2'-MDI: 2,2'-MDI=30~100%: 0~70%: 0~5%.

The dibasic alcohol in step a of the present invention is any one or a mixture of more than two of polyester dibasic alcohol, polyether dibasic alcohol, other dibasic alcohol or small molecule dibasic alcohol.

The polyester dibasic alcohol is polyethylene adipate-ethylene glycol-propylene glycol diol, polyethylene adipate-butylene glycol diol, poly sebacic acid-adipic acid-ethylene glycol-neopentyl glycol ester diol, polyethylene isophthalate-adipic acid-neopentyl glycol-diethylene glycol diol, polycarbonate diol or polycaprolactone diol.

The polyether polyol is a polyoxypropylene diol, polyoxyethylene-polypropylene oxide diol or polytetrahydrofuran dial.

The other dibasic alcohol is an amine ester diol, hydroxyl-terminated acrylic resin or hydroxyl-terminated alkyd resin.

The small molecule dibastic alcohol is a 3-methyl-1,5-pentanediol, neopentyl glycol, ethylene glycol, diethylene glycol, cyclohexanediol, methyl propanediol, TCD tricyclic diol, 1,3-propanediol, 1,4-bis(hydroxymethyl)cyclohexane, 1, 4-butanediol, 1,3-butanediol, 1,5-pentanediol, diethyl glutarate, 1,2-propanediol, diethylene glycol, tetrahydrofuran, 1,6-hexanediol, trimethyl pentanediol, butyl ethyl propanediol, 2,2-bis(4-hydroxyphenyl)propane, hydroxyl neopentanoic acid, neopentyl alcohol esters, resorcinol bis-hydroxyethyl ether, hydroquinone bis(2-hydroxyethyl)ether, resorcinol bis-hydroxypropyl ether, resorcinol bis-hydroxypropoxy ethyl ether, 2,5-di-tert-butyl hydroquinone, dipropylene glycol, tripropylene glycol, or ethyl hexanediol.

In step b of the present invention, the measured water is divided into a plurality of parts, where the water is deionized water or distilled water, and the plurality of parts are random 4~10.

According to the present invention, the organic solvent is an ester such as acetic ether, n-butyl acetate, ethylene glycol monoethyl ether acetate, propylene glycol monomethyl ether acetate, dimethyl carbonate, diethyl carbonate, diphenyl carbonate, acetone, methyl ethyl ketone, cyclohexanone, toluene, xylene, dioxane, tetrahydrofuran, N,N-dimethyl formamide, and a mixture of at least two thereof.

The molecular structure characteristic of the product of the present invention is to contain the dibasic alcohol modified MDI structure and the biuret structure at the same time. A chemical reaction formula (formula A) is used to demote the modified MDI structure (two substances reacted under specific conditions only have one product). The complex biuret structure is represented by the characteristic absorption peaks for the biuret structure in the infrared spectrogram of the laboratory sample of the present invention, where —NCO absorption peak is at the position of 2200 cm$^{-1}$, —NH— absorption peak is at the position of 3300 cm$^{-1}$, and —CO— absorption peak is at the position of 1750 cm$^{-1}$. Therefore, the product of the present invention is considered to include the biuret structure.

The present invention further aims at providing a dibasic alcohol modified MDI biuret curing agent series product. The introduction of the dibasic alcohol changes the performances of the MDI biuret curing agent. Some special performances may be designed according to the requirements of the users, for instance, increasing the pliability, rigidity, hardness and flexibility of the products given by the MDI curing agent as well as the compatibility with resins. Selecting different dibasic alcohols may manufacture a series of modified MDI biuret curing agents to satisfy the demands of various usages of polyurethane coatings and adhesive agents.

The modified MDI biuret curing agent of the present invention has excellent intermiscibility with supporting alkyd resin, polyurethane resin, acrylic resin, and the like.

The aromatic isocyanate biuret curing agent manufacturing technology of the present invention implements diversification and serialization of the MDI curing agent products, so that the MDI curing agent products may be popularized in each application field and replace the TDI curing agents more comprehensively.

Compared with the prior art, the present invention has the following advantages. I. The NCO weight percentage of the product is higher. The MDI biuret curing agent of the present invention improves the NCO percentage of the MDI prepolymer curing agent from 9~15% to 12~18%, which is equivalent to the NCO percentage of the TDI curing agent, thus satisfying the requirement of some special usages on the high NCO percentage of the polyurethane curing agent. II. The curing speed at a room temperature is slower. The modified biuret structure of the present invention reduces the activity of the free NCO groups and slows down the curing speed, thus satisfying the demands of some specific process conditions. III. The variety is diversified. The dibasic alcohol structure is introduced in the biuret molecular structure of the present invention, which makes the product structure diversified, enlarges the variety scope, and expands the usages. IV. The process is advanced. The circular reaction process of adding water by multiple times and reacting step-by-step at low and high temperature of the present invention improves the yield of mono molecule biuret and reduces the generation of polymers. V. The product viscosity is low. The viscosity of the present invention is low and the solid content of the present may reach 75%, which reduces the dosage of the organic solvent. VI. The storage stability is good. The present invention has excellent solvent diluting resistance and intermiscibility with resin components. The storage period of the present invention may last for more than half a year. The present invention improves the NCO percentage of the MDI curing agent, slows down the curing speed at a room temperature, and forms a new MDI curing agent variety, thus satisfying the demands of the polyurethane industry on different usages, different performances and different processes.

A desire of the present invention is to provide a modified diphenylmethane diisocyanate biuret curing agent having higher NCO weight percentage, slower curing speed at a room temperature, lower viscosity and fine storage stability so as to make up the defects of the prior art, thus satisfying the demands of different purpose and different performances of the polyurethane industry.

Another desire of the present invention is to provide a preparation method of the foregoing modified diphenylmethane diisocyanate biuret curing agent.

In FIG. 1, the laboratory sample of the invention is detected by using an infrared spectrometer, having a test result as illustrated in the FIG. 1. To implement the invention more preferably, the invention is further described hereinafter with references to the following embodiments as follows.

First Embodiment a, 125 g of MDI-100 (i.e. pure 4,4'-MDI), 125 g of MDI-50 (i.e. a mixture of 4, 2'-MDI occupying a weight of 50%, and 4,4'-MDI occupying a weight of 50%) and 80 g of n-butyl acetate are added into a reaction kettle, stirred uniformly, and reacted with 24.5 g of dehydrated tricyclic diol for 0.5 h at a room temperature, heated up to 60° C. and reacted for 2.5 hours at 65~75° C. to obtain an MDI-modified product;

b, the temperature is lowered to 70° C., and 1.1 g of water is added for the first time, reacted for 1.5 hours at 70~80° C., heated up to 120~130° C. and reacted for 1 hour; then the temperature is lowered to 80° C., and 1.1 g of water is added for the second time, reacted for 0.5 hour at 80~90° C., heated up to 120~130° C. and reacted for 0.5 hour; then the temperature is lowered to 80° C., and 1.1 g of water is added for the third time, reacted for 0.5 hour at 80~90° C., heated up to 120~130° C. and reacted for 0.5 hour; then the temperature is lowered to 80° C., and 1.2 g of water is added for the fourth time, reacted for 0.5 hour at 85~95° C., heated up to 120~130° C. and reacted for 0.5 hour; and then further heated up to 125~135° C. and reacted; during this period, sampling is performed in every 0.5 hour to test the NCO percentage; when the percentage is approaching to the theoretically designed value 12.0%, the temperature is lowered immediately to stop the reaction; and c, the temperature is lowered under 60° C., and 10 g of ethylene glycol monoethyl ether acetate is added, stirred uniformly, and then discharged, to obtain 358 g of modified MDI biuret curing agent which has a solid content of 75% and a viscosity of 2700 mpa·s (at 25° C.). The NCO content of the curing agent is 11.4% through testing (15.2% while being counted in terms of total solid).

Note: 1. The solid content is tested according to national standard GB/T 2793-1995 Test Method for Nonvolatile Content of Adhesives.

2. The NCO content is tested according to the Ministry of Chemical Industry's standard HG/T2409-92 Determination of the Isocyanate Group Content in Polyurethane Prepolymer.

3. The viscosity is tested according to the national standard GB/T 2794-1995 Determination Methods for Viscosity of Adhesives.

Second Embodiment a, 125 g of MDI-100, 125 g of MDI-50 and 76 g of n-butyl acetate are added into a reaction kettle, stirred uniformly, and reacted with 4 g of dehydrated neopentyl glycol and 4 g of diglycol for 0.5 hour at a room temperature, heated up to 60° C. and reacted for 1.5 hours at 70~80° C. to obtain an MDI-modified product;

b, the temperature is lowered to 70° C., and 1.2 g of water is added for the first time, reacted for 1 hour at 70~80° C., heated up to 120~130° C. and reacted for 0.5 hour; then the temperature is lowered to 80° C., and 1.2 g of water is added for the second time, reacted for 0.5 hour at 80~90° C., heated up to 120~130° C. and reacted for 0.5 hour; then the temperature is lowered to 80° C., and 1.2 g of water is added for the third time, reacted for 0.5 hour at 80~90° C., heated up to 120~130° C. and reacted for 0.5 hour; then the temperature is lowered to 80° C., and 1.2 g of water is added for the fourth time, reacted for 0.5 hour at 85~95° C., heated up to 120~130° C. and reacted for 0.5 hour; and then further heated up to 125~135° C. and reacted; during this period, sampling is performed in every 0.5 hour to test the NCO percentage; when the percentage is approaching to the theoretically designed value 13.5%, the temperature is lowered immediately to stop the reaction; and c, the temperature is lowered under 60° C., and 8 g of cyclohexanone is added, stirred uniformly, and then discharged, to obtain 335 g of modified MDI biuret curing agent which has a solid content of 75% and a viscosity of 2500 mpa·s (at 25° C.). The NCO content of the curing agent is 12.9% through testing (17.2% while being counted in terms of total solid).

Third Embodiment a, 250 g of MDI-100 and 112 g of n-butyl acetate are added into a reaction kettle, stirred uniformly, and reacted with 90 g of dehydrated polyethylene adipate-ethylene glycol-propylene glycol diol (having a molecular weight of 600) for 1 hour at a room temperature, heated up to 60° C., reacted for 2 hours at 70~80° C. to obtain an MDI-modified product;

b, the temperature is lowered to be under 70° C., and 1.0 g of water is added for the first time, reacted for 0.5 hour at 70~80° C., heated up to 120~130° C. and reacted for 0.5 hour; then the temperature is lowered to 70° C., and 1.0 g of water is added for the second time, reacted for 0.5 hour at 70~80° C., heated up to 120~130° C. and reacted for 0.5 hour; then the temperature is lowered to 70° C., and 1.0 g of water is added for the third time, reacted for 0.5 hour at 70~80° C., heated up to 120~130° C. and reacted for 0.5 hour; then the temperature is lowered to 90° C., and 1.0 g of water is added for the fourth time, reacted for 0.5 hour at 90~100° C., heated up to 120~130° C. and reacted for 0.5 hour; and then further heated up to 125~135° C. and reacted; during this period, sampling is performed in every 0.5 hour to test the NCO percentage; when the percentage is approaching to the theoretically designed value 9.7%, the temperature is lowered immediately to stop the reaction; and c, the temperature is lowered under 60° C., and then discharged, to obtain 446 g of modified MDT biuret curing agent which has a solid content of 75% and a viscosity of 3600 mpa·s (at 25° C.). The NCO content of the curing agent is 9.4% through testing (12.5% while being counted in terms of total solid).

Fourth Embodiment a, 250 g of MDI-100 and 107 g of n-butyl acetate are added into a reaction kettle, stirred uniformly, and reacted with 90 g of dehydrated polypropylene oxide glycol (having a molecular weight of 410) for 1 hour at a room temperature, heated up to 70° C., reacted for 1.5 hours at 80~90° C. to obtain an MDI-modified product;

b, the temperature is lowered to 70° C., and 1.2 g of water is added for the first time, reacted for 0.5 hour at 70~80° C., heated up to I20~130° C. and reacted for 0.5 hour; then the temperature is lowered to 70° C., and 1.2 g of water is added for the second time, reacted for 0.5 hour at 70~80° C., heated up to 120~130° C. and reacted for 0.5 hour; then the temperature is lowered to 80° C., and 1.3 g of water is added for the third time, reacted for 0.5 hour at 80~90° C., heated up to 120~130° C. and reacted for 0.5 hour; then further heated up to 125~135° C. and reacted; during this period, sampling is performed in every 0.5 hour to test the NCO percentage; when the percentage is approaching to the theoretically designed value 10.2%, the temperature is lowered immediately to stop the reaction; and c, the temperature is lowered under 60° C., and then discharged, to obtain 423 g of modified MDI biuret curing agent which has a solid content of 75% and a viscosity of 3100 mpa·s (at 25° C.). The NCO content of the curing agent is 10.0% through testing (13.3% while being counted in terms of total solid).

Fifth Embodiment a, 150 g of MDI-100, 100 g of MDI-50 and 76 g of n-butyl acetate are added into a reaction kettle, stirred uniformly, reacted with 12 g of dehydrated 3-methyl-1,5-pentanediol for 0.5 h at a room temperature, then heated up to 65~75° C. and reacted for 1 hour to obtain an MDI-modified product;

b, the temperature is lowered to 70° C., and 1.5 g of water is added for the first time, reacted for 1 hour at 70~80° C., heated up to 120~130° C. and reacted for 1 hour; then the temperature is lowered to 70° C., and 1.5 g of water is added for the second time, reacted for 0.5 hour at 75~85° C., heated up to 120~130° C. and reacted for 0.5 hour; then the temperature is lowered to 80° C., and 1.6 g of water is added for the third time, reacted for 0.5 hour at 80~90° C., heated up to 120~130° C. and reacted for 0.5 hour; and then further heated up to 125~135° C. and reacted; during this period, sampling is performed in every 0.5 hour to test the NCO percentage; when the percentage is approaching to the theoretically designed value 13.0%, the temperature is lowered immediately to stop the reaction; and c, the temperature is lowered under 60° C., and 5 g of methylbenzene and 5 g of cyclohexanone are added, stirred uniformly, and then discharged, to obtain 341 g of modified MDI biuret curing agent which has a solid content of 75% and a viscosity of 2200 mpa·s (at 25° C.). The NCO content of the curing agent is 12.4% through testing (16.5% while being counted in terms of total solid).

Sixth Embodiment a, 100 g of MDI-100, 150 g of MDI-50 and 100 g of n-butyl acetate are added into a reaction kettle, stirred uniformly, reacted with 12 g of dehydrated butylated dehydrated ethyl glycol for 0.5 h at a room temperature, then heated up to 60~70° C. and reacted for 1 hour; then 50 g of dehydrated polycaprolactone diol (having a molecular weight of 1000) is added, reacted for 1.5 hours at 65~75° C., and 1.5 hours at 80~85° C. to obtain an MDT-modified product;

b, the temperature is lowered to 70° C., and 1.5 g of water is added for the first time, reacted for 1.5 hours at 70~80° C., heated up to 120~130° C. and reacted for 1.5 hours; then the temperature is lowered to 70° C., and 1.5 g of water is added for the second time, reacted for 0.5 hour at 70~80° C., heated up to 120~130° C. and reacted for 0.5 hour; then the temperature is lowered to 80° C., and 1.5 g of water is added for the third time, reacted for 0.5 hour at 80~90° C., heated up to 120~130° C. and reacted for 0.5 hour; and then further heated up to 125~135° C. and reacted; during this period, sampling is performed in every 0.5 hour to test the NCO percentage; when the percentage is approaching to the theoretically designed value 10.2%, the temperature is lowered immediately to stop the reaction; and c, the temperature is lowered under 70° C., and 100 g of xylene and 105.5 g of propylene glycol ether acetate are added, stirred uniformly, and then discharged, to obtain 611 g of modified MDI biuret curing agent which has a solid content of 50%. The NCO content of the curing agent is 6.7% through testing (13.4% while being counted in terms of total solid).

First Application Embodiment

A coating film prepared by mixing 50 g of the product of embodiment 1 with 100 g of the hydroxyl radical components of alkyd resin coatings has the performances as follows: dryness: the surface drying time is 40 minutes and the hard drying time is 8 hours at 25° C.; the performances tested after three days are as follows: the lustre (60°) is ≥95%, the hardness is Shore D70, the impact strength is 528N.cm, the adhesive power is grade 1, and the pliability is 1 mm.

Test method: the lustre is tested according to GB9754-88, the hardness is tested according to GB1730~79, the impact strength is tested according to GB1732-93, the adhesive power is tested according to GB 1720-89, and the pliability is tested according to GB1731-79.

Second Application Embodiment

A coating film prepared by mixing 50 g of the product of embodiment 2 with 100 g of the hydroxyl radical components of alkyd resin coatings has the performances as follows: dryness: the surface drying time is 40 minutes and the hard drying time is 8 hours at 25° C.; the performances tested after three days are as follows: the lustre (60°) is ≥95%, the hardness is Shore D65, the impact strength is 580N.cm, the adhesive power is grade 1, and the pliability is 1 mm.

Third Application Embodiment 30 g of the product of embodiment 6 is mixed with 100 g of the hydroxyl radical components of polyurethane adhesives, for bonding and recombining a pure aluminum foil and a CPP film. After being cured for 48 hours at 50° C., a T peel strength test is carried out according to GB/T 2791-1995 Adhesives, T Peel Strength Test Method for a Flexible-to-flexible Test Specimen Assembly, and the peel strength is 1130 g/15 mm, and no separation phenomenon is found on the recombined film after going through a boiling test.

The invention claimed is:

1. A preparation method of modified diphenylmethane diisocyanate (MDI) biuret curing agent, comprising the steps of:
    a, adding MDI and an organic solvent in a reaction kettle, stirring uniformly, adding dehydrated dibasic alcohol for reaction at a room temperature for 0.5~2 hours, then heating up to 60° C., reacting at 60~90° C. for 1~4 hours to obtain an MDI-modified product;
    b, adding water by multiple times, wherein a molar ratio between the water and remaining MDI after the first step of the reaction is 1:3~3.2, wherein the water is added within a range from 4 to 10 times; controlling the temperature in the reaction kettle within 70~100° C., dropwise adding a first part of the water, and reacting for 0.5~2 hours, then heating up to 120~140° C. , and reacting for 0.5~2 hours; lowering the temperature to 70~100° C., dropwise adding a second part of the water, repeating the above process until all the water is added, reacting for 0.5~2 hours, heating up to 120~140° C. and reacting for 1~5 hours; and
    c, lowering the temperature to 60° C., adding the organic solvent according to the product solid content requirements, stirring uniformly, and discharging to obtain the modified MDI biuret curing agent;
    the feeding ratios of each reactant in the curing agent are as follows: in the first step of the reaction, the molar ratio between the dibasic alcohol and the MDI is 0.05~0.2:1; and in the second step of the reaction, the molar ratio between the water and the remaining MDI after the first step of the reaction is 1:3~3.2,
    wherein the mole number of the remaining MDI after the first step of the reaction is the difference of subtracting two times of the mole number of the dibasic alcohol from the MDI mole number fed in the first step of the reaction;
    the product indexes of the curing agent are as follows: wherein the following contents are weight percentages:
    (1) solid content: 50~75%; and
    (2) NCO content: 12~18%, counted in terms of total solid.

2. The preparation method of modified diphenylmethane diisocyanate (MDI) biuret curing agent according to claim 1, wherein the MDI is one or a mixture of at least two of 4,4'-MDI, 4,2'-MDI and 2,2'-MDI.

3. The preparation method of modified diphenylmethane diisocyanate (MDI) biuret curing agent according to claim 1, wherein the dibasic alcohol in step a is any one or a mixture of more than one of polyester dibasic alcohol, polyether dibasic alcohol, other dibasic alcohol or small molecule dibasic alcohol; wherein
    the other dibasic alcohol is an armine ester diol, hydroxyl-terminated acrylic resin or hydroxyl-terminated alkyd resin; and wherein
    the small molecule dibasic alcohol is a 3-methyl-1,5-pentanediol, neopentyl glycol, ethylene glycol, diethylene glycol, cyclohexanediol, methyl propanediol, TCD tricyclic diol, 1,3-propanediol, 1,4-bis (hydroxymethyl)cyclohexane, 1,4-butanediol, 1,3-butanediol, 1,5-pentanediol, diethyl glutarate, 1,2-propanediol, diethylene glycol, tetrahydrofuran, 1,6-hexanediol, trimethyl pentanediol, butyl ethyl propanediol, 2,2-bis (4-hydroxyphenyl) propane, hydroxyl neopentanoic acid, neopentyl alcohol esters, resoreinol bis-hydroxyethyl ether, hydroquinone bis (2-hydroxyethyl) ether, resoreinol bis-hydroxypropyl ether, resorcinol bis-hydroxypropoxy ethyl ether, 2,5-di-tert-butyl hydroquinone, dipropylene glycol, tripropylene glycol, or ethyl hexanediol.

4. The preparation method of modified diphenylmethane diisocyanate (MDI) biuret curing agent according to claim 3, wherein the polyester dibasic alcohol is polyethylene adipate-ethylene glycol-propylene glycol diol, polyethylene adipate-butylene glycol diol, poly sebacic acid-adipic acid-ethylene glycol-neopentyl glycol ester diol, polyethylene isophthalate-adipic acid-neopentyl glycol-diethylene glycol diol, polycarbonate diol or polycaprolactone diol.

5. The preparation method of modified diphenylmethane diisocyanate (MDI) biuret curing agent according to claim 3, wherein the polyether glycol is a polyoxypropylene diol, polyoxyethylene-polypropylene oxide diol or polytetrahydrofuran diol.

6. The preparation method of modified diphenylmethane diisocyanate (MDI) biuret curing agent according to claim 1, wherein the organic solvent is an ester such as acetic ether, n-butyl acetate, ethylene glycol monoethyl ether acetate, propylene glycol monomethyl ether acetate, dimethyl carbonate, diethyl carbonate, diphenyl carbonate, acetone, methyl ethyl ketone, cyclohexanone, toluene, xylene, dioxane, tetrahydrofuran, N, N-dimethyl formamide, and a mixture of at least two thereof.

\* \* \* \* \*

UNITED STATES PATENT AND TRADEMARK OFFICE
CERTIFICATE OF CORRECTION

PATENT NO. : 9,505,910 B2
APPLICATION NO. : 14/352232
DATED : November 29, 2016
INVENTOR(S) : Zhou et al.

It is certified that error appears in the above-identified patent and that said Letters Patent is hereby corrected as shown below:

In the Claims

Column 12, Claim 3, Line 54, "armine" should be --amine--.

Column 12, Claim 3, Line 67, "resoreinol" should be --resorcinol--.

Column 13, Claim 3, Line 1, "resoreinol" should be --resorcinol--.

Signed and Sealed this
Fifth Day of February, 2019

Andrei Iancu
*Director of the United States Patent and Trademark Office*